US00PP10189P

United States Patent [19]

Olij

[11] Patent Number: Plant 10,189

[45] Date of Patent: Jan. 13, 1998

[54] HYBRID TEA ROSE PLANT NAMED 'OLIJZOUC'

[75] Inventor: Huibert W. Olij, De Kwakel, Netherlands

[73] Assignee: Olij Rosen-B.V., De Kwakel, Netherlands

[21] Appl. No.: 723,310

[22] Filed: Sep. 30, 1996

[51] Int. Cl.[6] ..... A01H 5/00

[52] U.S. Cl. ..... Plt./21

[58] Field of Search ..... Plt./20, 21

[56] References Cited

U.S. PATENT DOCUMENTS

P.P. 7,749 12/1991 Pekmez ..... Plt./21

P.P. 7,902 7/1992 Marciel ..... Plt./21

P.P. 7,922 7/1992 Marciel ..... Plt./21

P.P. 7,932 8/1992 Marciel ..... Plt./21

*Primary Examiner*—Howard J. Locker

*Attorney, Agent, or Firm*—Burns Doane, Swecker & Mathis, L.L.P.

[57] ABSTRACT

A new and distinct variety of Hybrid Tea rose plant is provided which abundantly forms attractive double Currant Red blossoms having very strong petals. Such blossoms are long-lasting on the plant or when cut and placed in a vase and exhibit good petal-drop characeristics. The plant exhibits long very erect stems and forms attractive deep green foliage. The new variety is particularly well suited for cut flower production under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Korlift' variety (non-patented in the United States). The 'Korlift' variety sometimes is known as the 'Sylvia' variety. The male parent (i.e., the pollen parent) was the product of the pollination of the 'Korbeen' variety (non-patented in the United States) and the 'Transelbon' variety (non-patented in the United States). The parentage of the new variety can be summarized as follows:

'Korlift'×('Korbeen'×'Transelbon').

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characeristics:

(a) forms in abundance attractive double long-lasting Currant Red blossoms having very strong petals,
(b) forms very erect stems,
(c) forms attractive deep green and glossy foliage, and
(d) is particularly well suited for cut flower production.

The new variety well meets the needs of the horticultural industry and is particularly well adapted for cut flower production under greenhouse growing conditions.

The new variety has been found to undergo asexual propagation in France by a number of routes, including budding, grafting, and cuttage. Asexual propagation by the above-mentioned techniques in France has shown the the characteristics of the new variety are stable and are strictly transmissible by such asexual propagation from one generation to another.

The new variety has been named the 'Olijzouc' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during February while budded on *Rosa indica* understock and growing in greenhouses at Le Cannet des Maures, Var, France. Dimensions in centimeters are indicated at the bottom of the photograph.

DETAILED DESCRIPTION

Figures 1, 2, 3, 4, 5, 6, 7, 8, 9, 10, 11, 12, 13, 14, 15, 16:
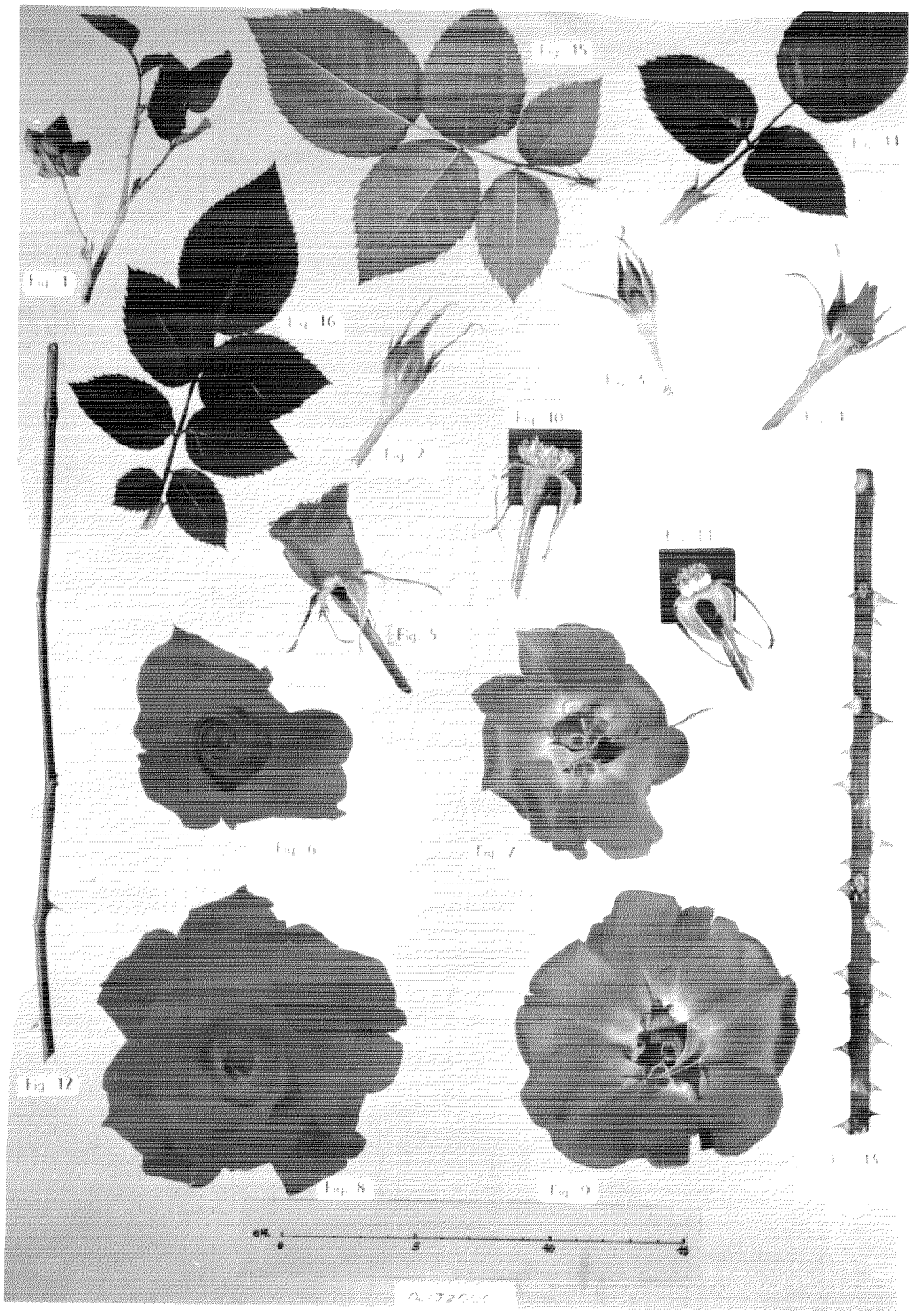
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — upper surface.
FIG. 15 illustrates a specimen of a leaf with five leaflets — plan view — under surface.
FIG. 16 illustrates a specimen of a leaf with seven leaflets — plan view — upper surface.

The chart used in the identification of the colors is that of The Royal Horticultural Society (R.H.S. Colour Chart). The description is based on the observation of three year-old plants during February while budded on *Rosa indica* understock and growing in greenhouses at Le Cannet des Maures, Var, France. The coloration in common terms precedes reference to the chart in some instances.

Class: Hybrid Tea.

Plant:

*Height.*—When pruned to a height of 85 cm., floral stems of approximately 50 to 70 cm. in length commonly are formed.

*Habit.*—Erect.

Branches:

*Color.*—Young stems: Yellow-Green Group 144A. Adult wood: Green Group 137B.

*Thorns.*—Size: medium. Quantity: somewhat numerous. Color: yellowish (as illustrated).

Leaves:

*Stipules.*—Adnate, pectinate, broad and linear.

*Petioles.*—Upper surface: striped reddish brown on young foliage, and green on adult foliage. Under surface: light green, and smooth.

*Leaflets.*—Number: 3, 5 (most often), and 7. Shape: elliptic. Serration: single and regular. Texture: consistent. General appearance: dense, dark green, and very bright. Color (young foliage): Upper surface: near Yellow-Green Group 144A and suffused with reddish brown. Under surface: dark green, near Yellow-Green Group 144A, and suffused with reddish brown. Color (adult foliage): Upper surface: near Green Group 139A. Under surface: near Greyed-Green Group 191A.

Inflorescence:

*Number of flowers.*—Usually one to three per stem.

*Peduncle.*—Medium green in coloration and the length is approximately 10 cm. on average.

*Sepals.*—Upper surface: tomentose, and greenish in coloration. Under surface: medium green in coloration and commonly possess very few extensions.

*Bud.*—Shape: conical. Length: approximately 5 cm. on average. Size: medium. Color upon opening: Upper surface: Currant Red, near Red Group 46A. Under surface: Currant Red, near Red Group 47A.

*Flower.*—Shape: cup-shaped with parallel sides. Diameter: approximately 12 cm. on average. Color (when opening begins): Upper surface: Currant Red, near Red Group 46A. Under surface: near Greyed-Purple Group 185A with some whitening on the external petals. Color (when blooming): Upper surface: Currant Red, near Red Group 46A. Under surface: Currant Red, near Red Group 47A with some whitening on the external petals. Color (at end of opening): Upper surface: Currant Red, near Red Group 46A. Under surface: Currant Red, near Red Group 47A with some whitening on the external petals. Fragrance: none. Lasting quality: long on the plant and when cut and placed in a vase with the blossoms commonly lasting approximately 10 to 12 days in each instance. Petal number: approximately 35 on average. Petal shape: rounded with undulating edges. Petal drop: very good with the petals commonly detaching cleanly. Stamen number: approximately 200 on average. Anthers: normal golden yellow in coloration. Filaments: reddish in coloration. Pistils: approximately 150 on average. Stigmas: yellowish in coloration. Styles: pinkish in coloration. Receptacle: medium green, smooth, and in longitudinal section in the shape of a pitcher. Hips: hips and seeds are formed.

Development:

*Vegetation.*—Strong.

*Blooming.*—Abundant with approximately 150 to 170 blooms per square meter commonly being formed per year.

*Resistance to disease.*—Very good.

I claim:

1. A new and distinct variety of Hybrid Tea rose plant characterized by the following combination of characteristics:

(a) forms in abundance attractive double long-lasting Currant Red blossoms having very strong petals,
(b) forms very erect stems,
(c) forms attractive deep green and glossy foliage, and
(d) is particularly well suited for cut flower production;

substantially as herein shown and described.

* * * * * cm.
0
5
10
15